(12) United States Patent
Johannison

(10) Patent No.: US 11,919,190 B2
(45) Date of Patent: Mar. 5, 2024

(54) PROCESS FOR INTRODUCING PERFORATIONS INTO LAMINATES COMPRISING SILICONE GELS

(71) Applicant: Mölnlycke Health Care AB, Gothenburg (SE)

(72) Inventor: Ulf Johannison, Landvetter (SE)

(73) Assignee: Mölnlycke Health Care AB, Gothenburg (SE)

( * ) Notice: Subject to any disclaimer, the term of this patent is extended or adjusted under 35 U.S.C. 154(b) by 392 days.

(21) Appl. No.: 17/433,686

(22) PCT Filed: Feb. 24, 2020

(86) PCT No.: PCT/EP2020/054735
§ 371 (c)(1),
(2) Date: Aug. 25, 2021

(87) PCT Pub. No.: WO2020/173856
PCT Pub. Date: Sep. 3, 2020

(65) Prior Publication Data
US 2022/0152861 A1    May 19, 2022

(30) Foreign Application Priority Data
Feb. 26, 2019    (EP) ..................................... 19159465

(51) Int. Cl.
*B26F 1/24*    (2006.01)
*B26D 7/08*    (2006.01)
*B29C 65/00*    (2006.01)

(52) U.S. Cl.
CPC ................ *B26F 1/24* (2013.01); *B26D 7/086* (2013.01); *B29C 66/02242* (2013.01)

(58) Field of Classification Search
CPC .......... B26F 1/24; A61F 13/02; A61F 13/025; A61F 13/0253; A61F 13/0283;
(Continued)

(56) References Cited

U.S. PATENT DOCUMENTS

| 4,747,895 A | 5/1988 | Wallerstein |
| 9,737,631 B2 | 8/2017 | Hansson |

(Continued)

FOREIGN PATENT DOCUMENTS

| EP | 1 112 823 | 7/2001 |
| EP | 2 382 069 | 11/2011 |

(Continued)

OTHER PUBLICATIONS

International Preliminary Report on Patentability dated Aug. 25, 2021 by the International Searching Authority for Application No. PCT/EP2020/054735 which was filed on Feb. 24, 2020 and published as WO/2020/173856 on Sep. 3, 2020 (Applicant—Mölnlycke Health Care AB // Inventor: Johannison.) (7 pages).

(Continued)

*Primary Examiner* — Nahida Sultana
*Assistant Examiner* — Mohamed K Ahmed Ali
(74) *Attorney, Agent, or Firm* — Ballard Spahr LLP

(57) ABSTRACT

Described is a process for introducing perforations in a laminate that comprises a silicone gel. The process includes the following steps: bringing an array of perforating elements in contact with a deformable layer of a laminate that at least includes a substrate layer, a layer comprising a silicone gel and a deformable layer, wherein said deformable layer covers said layer including the silicone gel; applying ultrasonic energy to said laminate in order to simultaneously introduce a plurality of perforations into said laminate, while providing deformed portions in said deformable layer, wherein said deformed portions penetrate into the plurality of perforations in said laminate; after having introduced said plurality of perforations into said laminate, keeping said deformable layer in contact with said layer including the silicone gel, such that said deformed portions remain pen- (Continued)

etrating into said plurality of perforations, for at least 12 hours.

13 Claims, 5 Drawing Sheets

(58) Field of Classification Search
CPC ........... B32B 3/10; B32B 3/266; B32B 27/32; B32B 27/40; B32B 38/04
See application file for complete search history.

(56) References Cited

U.S. PATENT DOCUMENTS

2010/0307513 A1 12/2010 Svensby
2011/0229688 A1* 9/2011 Cotton .................... B32B 27/40
428/138

FOREIGN PATENT DOCUMENTS

| EP | 2 561 843 | 2/2013 |
| WO | WO 2009/031948 | 3/2009 |
| WO | WO 2010/061228 | 6/2010 |
| WO | WO 2018/172414 | 9/2018 |

OTHER PUBLICATIONS

International Search Report and Written Opinion issued in PCT/EP2020/054735 dated May 26, 2020 (Applicant—Mölnlycke Health Care AB) (10 pages).

* cited by examiner

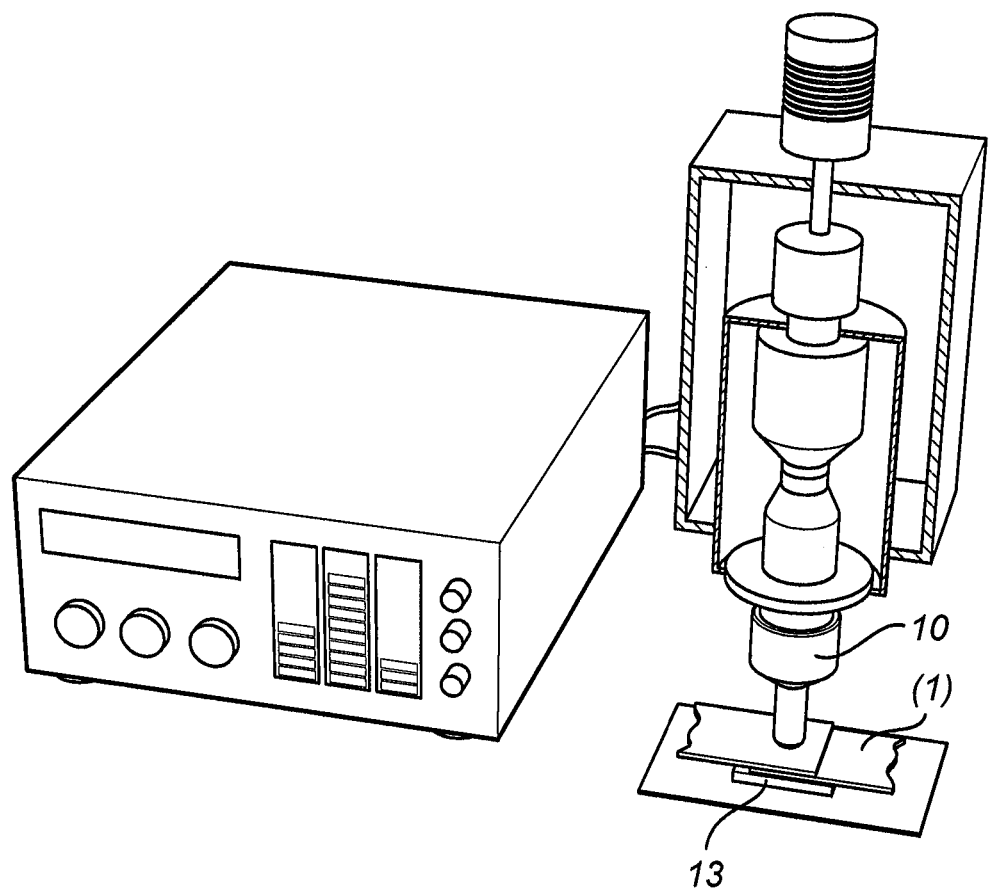
Fig. 1
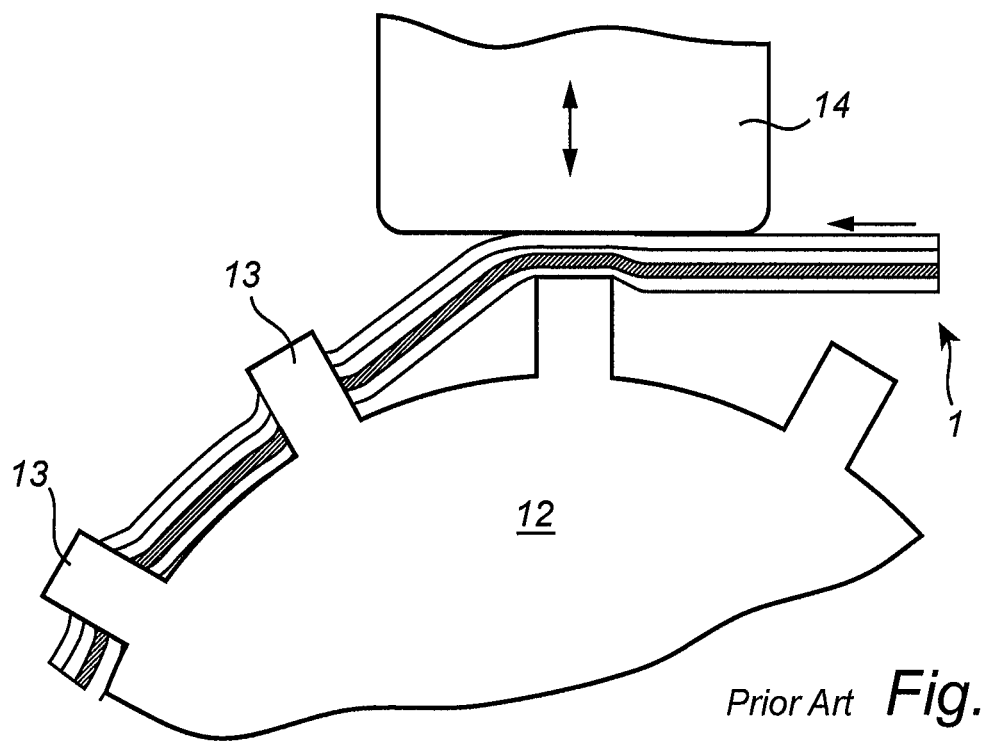
Prior Art Fig. 2

PROCESS FOR INTRODUCING PERFORATIONS INTO LAMINATES COMPRISING SILICONE GELS

CROSS-REFERENCE TO RELATED APPLICATIONS

This application is a U.S. National Phase Application of International Application No. PCT/EP2020/054735, filed Feb. 24, 2020, which claims priority to European Application No. 19159465.4, filed Feb. 26, 2019, each of which are hereby incorporated by reference in their entirety.

FIELD OF THE INVENTION

The present invention relates to a process for the introduction of perforations into a laminate comprising a silicone gel, more particular to the use of ultrasonic energy to create stable perforations in a laminate that comprises a silicone gel.

In particular, the process according to the present invention comprises the following steps: (iii) bringing an array of perforating elements in contact with a deformable layer of a laminate that at least comprises a substrate layer, a layer comprising a silicone gel and a deformable layer, wherein said deformable layer covers the silicone gel (iv) applying ultrasonic energy to said laminate in order to simultaneously introduce a plurality of perforations into said laminate, while introducing deformed portions in said deformable layer, wherein said deformed portions essentially correspond to the shape of the perforating elements, further wherein said deformed portions at least partly penetrate into the perforations so created; (v) after having introduced said plurality of perforations into said laminate, i.e. after step (iv), keeping said deformable layer in contact with said silicone layer, such that said deformed portions remain penetrating into said plurality of perforations, for at least 12 hours, preferably at least 24 hours, further preferably at least 36 hours, further preferably at least 48 hours.

The primary purpose of keeping said deformable layer in contact with said silicone layer is to avoid, or at least minimize, the adverse effect of at least part of the silicone gel occluding the perforations created. Without wishing to be bound by theory, the inventors believe that silicone gel that is at least partly cured strives to "move back" to its "original" physical shape, i.e. to its position prior to the perforation step, due to crosslinking chemical bonds formed during the curing process,.

BACKGROUND OF THE INVENTION

Ultrasonic welding is known as a suitable technique for joining or modifying complex parts or structures, including laminates of materials that comprise at least one thermoplastic layer. Several process steps can be carried out in a single step, including welding, cutting and perforating. The parts or layers to be joined or modified [e.g. a laminate (1)], in particular to be perforated, are typically sandwiched between a perforating element (13) and a sonotrode (horn) (10), connected to a transducer (see FIG. 1 for a schematic drawing of such an ultrasonic welding device). Typically, a ~20 kHz low-amplitude acoustic vibration is emitted (other common frequencies used in ultrasonic welding of thermoplastics are 15 kHz, 20 kHz, 30 kHz, 35 kHz, 40 kHz and 70 kHz). The ultrasonic energy (locally) melts the point contact between the parts, creating a joint (or, depending on the energy input and contact time, a hole).

Ultrasonic welding specifically for the purposes of creating perforations in a laminate is known, in principle, for example from U.S. Pat. No. 4,747,895, which discloses the ultrasonic perforating of a continuously moving strip of materials (for example an adhesive-backed plastic strip). In accordance with U.S. Pat. No. 4,747,895, the continuously moving strip passes through a gap defined by an ultrasonic horn and is brought in contact with a rotating drum that has sharp perforating projections acting as an array of anvils.

This basic principle is more specifically applied to a laminate that comprises silicone gel in EP 2 382 069. The perforating elements according to EP 2 382 069 are realized as pin-like projections with a flat top (13), arranged on a rotating drum (12). The laminate (1) is continuously fed through the gap created between the sonotrode (14) and the perforating elements (13) (see FIG. 2).

Similarly, EP 1 112 823 discloses a web perforation method using a rotating drum ("pin roll") with pin-like perforation elements in an ultrasonic device.

One potential drawback of the process of ultrasonic perforating is that a material present in the laminate that is not thermoplastic (i.e. does not necessarily retain its shape after melting and cooling), for example the silicone gel as described in EP 2 382 069, may be squeezed to the edges of the hole and may (partially) occlude the perforation, i.e. may over time (i.e. hours) at least partially move back towards its "original" position (prior to perforation). This problem is perhaps best illustrated in FIG. 6*a*, which shows a perforated laminate comprising silicone gel that is perforated according to the processes known from the art. From FIG. 6*a*, it is apparent that the original perforation as defined by the out-perforated substrate layer is partly occluded by silicone gel, striving to adopt its "original" position, i.e. the position prior to perforation.

SUMMARY OF THE INVENTION

In view of the above-mentioned or other drawbacks or unfulfilled needs of the prior art, one object of the present invention is to provide a process for introducing perforations into a laminate, wherein said laminate comprises a layer of silicone gel, which process minimizes or avoids the occurrence of occlusion of perforations introduced into laminates.

This object or these objects, and others, is/are solved by a process for introducing a plurality of perforations into a laminate, wherein said process comprises at least the following steps:
i. providing a laminate, said laminate comprising at least one substrate layer, said substrate layer being in contact with at least one layer comprising a silicone gel;
said laminate further comprising, in contact with said silicone gel layer, at least one deformable layer;
ii. providing an ultrasonic welding device comprising an array of perforating elements suitable for introducing perforations into at least said substrate and said layer comprising silicone gel;
iii. bringing said array of perforating elements in contact with said laminate, in particular with said deformable layer;
iv. applying ultrasonic energy to said laminate in order to simultaneously introduce a plurality of perforations into at least said substrate and said layer comprising silicone gel, while introducing deformed portions in said deformable layer, wherein said deformed portions essentially correspond to the shape of the perforating elements, further wherein said deformed portions at least partly penetrate into the perforations so created;

v. after having introduced said plurality of perforations into said laminate, i.e. after step (iv), keeping said deformable layer in contact with said layer comprising silicone layer, such that said deformed portions remain penetrating into said plurality of perforations, for at least 12 hours, preferably at least 24 hours, further preferably at least 36 hours, further preferably at least 48 hours;

vi. optionally, after the time period indicated in step (v), removing said deformable layer from the layer comprising silicone gel.

In accordance with the present invention, a "laminate" is a composite material comprising at least three layers that are joined to each other by way of adhesion, heat, pressure or any combination thereof.

Any number or kind of further layer(s) may be present, as long as these additional layer(s) do not significantly interfere with the perforation steps in accordance with the present invention. Any layer, for example an absorbent layer, a release liner, a fiber layer for distributing liquid or any further structural layer, or any other layer as commonly used in and suitable for wound treatment is preferred in that context.

The present invention is partly based on the realization that cross-linked (i.e. at least partially or essentially fully cured) silicone gel that is part of said laminate, is generally at least partly squeezed to the edges of the perforation created during perforation (cross-linked silicone gel generally does not melt upon exposure to ultrasonic energy input but rather softens and is "pushed away"). Subsequently, this silicone gel may (partially) occlude the perforation, i.e. may, over time (e.g. hours), at least partially "move back" towards its "original" position (prior to perforation).

The inventors have realized that this partial "moving-back" into its original position by (fully or partially cross-linked) silicone gel is essentially independent of how the ultrasonic energy input is controlled, in particular independent of for how long the perforation element is in contact with the laminate to create the perforation. In other words, even if the actual perforation step and ultrasonic energy input is in the range of seconds, the problem of occlusion still occurs.

Without wishing to be bound by theory, the inventors believe that, generally, silicone gel that is at least partly cured strives to "move back" to its original physical shape due to crosslinking chemical bonds formed during the curing process, i.e. prior to the perforation step.

This problem is perhaps best illustrated in FIG. 6a, which shows a perforated laminate comprising silicone gel that was perforated according to the processes known from the art. From the Figures, in particular from FIG. 6a, it is apparent that the original perforation as defined by the out-perforated substrate layer is partly occluded by silicone gel, striving to adopt its "original" position, i.e. the position prior to perforation.

The inventors have further found that this process of occlusion is relatively slow and may occur long after the actual step of creating the perforation. Thus, the problem occlusion cannot be suitably solved during the perforation step, for example by varying the boundary conditions and/or perforation time.

The present invention is further partly based on the realization that a deformable layer may be used to avoid occlusion of perforations made in an at least partly cured silicone gel layer. By introducing a deformable layer that is in contact with the silicone gel layer and the perforating elements during the perforation process, the perforating elements can provide imprints ("deformed portions") in the deformable layer, which imprints essentially correspond to the shape of the perforating elements, and thus the imprints can at least partly, preferably essentially completely penetrate into, and fill out, the perforations. In contrast to the perforation elements, which are removed instantly after the perforation step in a continuous process, the deformable layer having imprints can be kept in direct contact with the silicone layer long after the perforation step, thereby ensuring that the perforations are kept open and any occlusion of the perforations in the layer comprising silicone gel (i.e. by movement of the surplus silicone gel material accumulated around the edges of each perforation) is thus substantially avoided, or at least minimized.

Accordingly, the primary purpose of keeping the deformable layer in contact with the silicone layer is to avoid, or at least minimize, the effect of at least parts of the silicone gel occluding the perforations as just created. As already outlined above and without wishing to be bound by theory, the inventors believe that silicone gel, that is at least partly cured prior to the perforation step, or silicone gel that is essentially completely cured, strives to "move back" to its "original" position due to chemical crosslinking, which occurs during the curing process.

Substrate Layer

In embodiments of the present invention, said substrate layer of the laminate is a film of a polymer layer, preferably the layer comprising at least one thermoplastic polymer material.

Preferred thermoplastic polymers are polyurethane, polyethylene, ethylene vinyl acetate, polypropylene, polyvinyl chloride, polystyrol, polyether, polyester, polyamide, polycarbonate, polyether polyamide copolymers, polyacrylate, polymethacrylate, and/or polymaleate. Preferably, the thermoplastic polymers are elastomeric. In preferred embodiments of the present invention, the substrate layer comprises polyurethane, polyethylene or ethylene vinyl acetate. In accordance with the present invention, any substrate layer or combination substrate sublayers may be used, as long as these layer(s) is/are suitable to be perforated in accordance with the present invention. In particular, the substrate layer must be suitable to support silicone gel during perforation and also at the point-of-use of the laminate (preferably in or as wound treatment).

In embodiments of the present invention, the thickness of said substrate layer is from 5 μm to 200 μm, preferably from 10 μm to 100 μm, further preferably from 15 μm to 60 μm.

Being "thermoplastic" is generally understood to be the property of a polymer material to repeatedly soften upon application of heat and to repeatedly harden when cooled down, within a temperature range that is typical for the respective material, wherein the material remains capable of being formed, in the softened stage, in particular repeatedly so, by way of flowing, for example into a shaped article, extruded or otherwise shaped.

In embodiments of the present invention, the substrate layer may be in contact with at least one further layer that is positioned farther away from the silicone gel layer, i.e. situated behind (i.e. "above", see FIG. 4) the substrate layer. In embodiments, said additional layer may comprise an absorbent body.

In other embodiments said further layer is a paper layer.

In preferred embodiments, said at least one further layer is not perforated.

In embodiments of the present invention, a silicone composition, precursor or silicone gel is brought into contact, in particular joined with the substrate layer in a process step (0)

that occurs prior to step (i). Preferably, said bringing into contact/joining a silicone composition, precursor or silicone gel with the substrate layer occurs in a continuous manner.

Silicone Gel

Silicone gels as used in the laminates and in the process of the present invention are known in the art (see e.g. WO2009/031948), in particular for use as adhesives and/or wound contact surfaces in wound care. Specifically, silicone gels are understood to be gentle on the skin, in contrast to harder adhesives, e.g. acrylic adhesives. This is because a soft silicone gel can follow the contours of the skin well thus providing a large contact surface area. Thus, although the actual adhesive force in each contact point of a silicone gel adhesive generally is less than that of a typical acrylic adhesive, the large surface area of contact achieved with a silicone gel affords a high overall adherence to the skin, whilst at the same time, the silicone gel is skin-friendly, i.e. when a silicone gel silicone gel is removed from the skin very few skin cells are co-removed due to the comparatively low adhesive force in each contact point. Therefore, the problem of skin stripping can be avoided or minimized.

In preferred embodiments, the silicone gel comprises or is a two-component addition-hardening silicone gel, i.e. the curing process (only) starts when the two components are joined with the substrate, in particular in step (0) as outlined above.

Such a two-component silicone gel may be a chemically crosslinked silicone gel, for example a polydimethyl siloxane gel, for instance a platinum catalyzed 2-component addition hardening RTV-silicone. Examples of gels that can be used are SilGel 612 from Wacker-Chemie GmbH, Burghausen, Germany, and MED-6340 from NuSil Technology, Carpinteria, USA. Examples of silicone gel gels useful in this context are also described in GB-A-2 192 142, GB-A-2 226 780 and EP-A1-0 300 620.

In preferred embodiments of the present invention, the silicone gel is a two-component silicone gel and the time from the moment of joining the substrate layer with the silicone gel in a step (0) and the moment of applying ultrasonic energy to the laminate in order to simultaneously introduce a plurality of perforations into said laminate is not more than 12 hours, preferably no more than 6 hours.

If perforations are introduced after more than 24 h after coating of the silicone gel onto the sabatrate layer in a step (0) (starting of the curing process), the inventors have found that the silicone gel will have a higher tendency to "move back" into its original shape (and occlude the PU perforations), in which case the "deformed" film must be kept in place for longer time (>48 h) before being removed (e.g. during conversion into a dressing). Without wishing to be bound by theory, this effect is believed to be due to post-curing, i.e. even 24 h after coating (at which time the components of the silicone are mixed and curing is started) slow post-curing reaction is still occuring which results in even higher crosslinking (thus more tendency to "move back").

One purpose of step (v), i.e. the step in which the deformable layer is kept in contact with the layer comprising silicone gel, wherein the deformed portions (or imprints) of the deformable layer penetrate into the perforations in the layer comprising silicone gel, is to minimize occlusion of the perforations, that is, movement of surplus silicone gel that has been accumulated around the edges of the perforations is minimized.

Without wishing to be bound by theory, the tendency of silicone gel to move back to its original (non-perforated) position, and thus the need of having the deformable film for a period of time post-perforation, is believed to be related to the degree of crosslinking of the silicone. The inventors have found that, generally, the more the silicone gel has crosslinked ("cured") prior to the introduction of the perforations, the longer the deformable layer needs to be kept in place.

In embodiments of the present invention, the softness/penetration depth of the silicone gel is from 3 mm to 20 mm, preferably from 4 mm to 17 mm, further preferably from 9 mm to 15 mm.

As outlined below when discussing the Figures/Examples, the inventors have found that the strongest effect of occlusion, and therefore a particular need to avoid the same by using the process according to the present invention, occurs for silicone gels that have comparatively low softness (penetration) values, in particular from 3 mm to 15 mm.

Without wishing to be bound by theory, it is believed that this effect is related to the higher degree of crosslinking in harder silicone as compared to softer silicone. This behaviour may seem to be counter-intuitive to the skilled person as the skilled person would initially expect that softer silicone gels have a higher tendency to "flow".

The method for measuring the softness/penetration of s silicone gel is described, for example in U.S. Pat. No. 9,737,631, the respective content of which is hereby incorporated by reference.

This method used for measuring the softness/penetration of silicone gel is performed in accordance with the standards ASTM D 937 and DIN 51580, however deviates in a few defined steps which are explained below. FIGS. 3a-b illustrate this modified method for measuring softness in a silicone gel by letting a cone B having a weight of 62.5 g penetrate a test specimen C by gravity, said specimen being made of the silicone gel, the softness of which is to be determined, and having a thickness of 30 mm. The test specimen is obtained by filling a cylindrical container having an inner diameter of 60 mm and an inner height of 35-40 mm, with silicone gel up to a height of 30 mm.

When testing a silicone gel, uncured silicone pre polymer is filled into the container, and this pre polymer will then crosslink into a gel in the container. The cone used is shown in FIG. 3 and has the following dimensions: a=65 mm, b=30 mm, c=15 mm and d=8.5 mm. The method for determining softness includes lowering of the cone B to a position, indicated with dashed lines, in which the tip of the cone just touches the surface of the test specimen C. The cone B is then released so that it is allowed to penetrate the test specimen C due to gravity. The extent of penetration, i.e. the distance by which the cone has penetrated the test specimen in mm is measured after 5 seconds, and represents the penetration value P, which is the larger, the softer the test specimen is.

A penetrometer PNR 10 from Sommer & Runge K G, Germany, is used in the method.

In embodiments of the present invention, the "grammage" (amount of silicone gel per square meter) is from 10 $g/m^2$ to 500 $g/m^2$, preferably from 15 $g/m^2$ to 200 $g/m^2$. The inventors have found that occlusion is more difficult to prevent or minimize if the grammage is too high, for example above 500 $g/m^2$.

"Deformable Layer"

In embodiments of the invention, the deformable layer is preferably adapted such that it does not melt under the ultrasonic energy input as provided in the perforation process. Thereby, deformed portions, or imprints, corresponding to the perforating elements may be provided without breaking the deformable film (e.g. by creating perforations therein or by complete loss of material).

In embodiments of the invention, the melting point of the deformable layer is from 120 to 220° C., preferably from 130 to 190° C.

In embodiments of the invention, the deformable layer comprises or is a material selected from polypropylene, polyester, polycarbonate or polyamide.

In embodiments of the present invention, the thickness of the deformable layer is from 30 μm to 120 μm, preferably from 40 μm to 80 μm.

In embodiments of the invention a process aiding film is provided, wherein the process aiding film is arranged between the deformable layer and the silicone gel layer. For exampe, a film of polyethylene may be used as a process aiding film to be arranged in between a film of polyamide (deformable layer) and the silicone gel layer wherein the film of polyethylene functions as a release liner against the silicone gel layer.

"Perforating Elements"

The shape, outline, realization or arrangement of the perforation element(s) is of no particular relevance to the working of the present invention as the deformable film can follow the shape of essentially any perforation element or array thereof. Therefore, in accordance with the present invention, the perforation element can be of essentially any form or shape that renders the perforation element suitable to perforate a layer comprising silicone gel and at least one further layers In embodiments of the present invention, the perforating element(s) is/are pin-like elevations on a supporting element. In embodiments of the invention, said supporting element is a rotating drum.

In embodiments of the present invention, the outer side of the perforation element(s) is/are slanted, i.e. the perforation element(s) is/are essentially conically shaped.

Perforations

In embodiments of the present invention, the perforations have a diameter of from 0.5 mm to 20 mm, preferably from 0.75 mm to 4 mm.

While the perforations preferably are essentially circular, any other conceivable shape of the peroration is also within the scope of the present invention. In this case, the maximum width of such a shape is equivalent to the diameter as outlined above.

In embodiments of the present invention, the fact that a "plurality" of perforations is introduced into the laminate in step (iv) means that at least 12 perforations are formed simultaneously, preferably at least 24, further preferably 48.

In accordance with the present invention, and in particular in the claims, the terms "comprising" and "comprise(s)" do not exclude other elements or steps. Use of the indefinite article "a" or "an" does not exclude a plurality of elements or steps.

The mere fact that certain measures are recited in mutually different dependent embodiment or claims does not indicate that a combination of these measures cannot be used to advantage.

DESCRIPTION OF THE FIGURES

FIG. 1: schematically shows an ultrasonic welding device comprising, among others, a sonotrode/horn (10) and an opposed perforation element (13) that can be used to introduce perforations into a laminate (1).

FIG. 2: shows an apparatus known from the art for continuously introducing perforations into a laminate. A rotating drum (12) comprising perforation elements (13), in conjunction with the sonotrode (14), introduces perforations into a laminate (1).

Figure 5A:
FIGS. 5A-C: show a microscopic image of a perforated laminates having the layer structure as schematically shown in FIG. 4 [polyurethane substrate layer ("PU film") and silicone coating], wherein, in FIG. 5A, the silicone layer has a grammage of 500 g/m2 and a comparatively high softness/penetration depth of 14.5 mm and the deformable film [laminate of polyethylene (PE) film and polyamide (PA) film, wherein the PE film functions as a processing aid, i.e. release liner against the silicone and the PA film is the deformable film] as deformed (having deformed portions that penetrate into the perforations) was removed immediately after the perforating step (process not in accordance with the present invention).
Figure 5B:
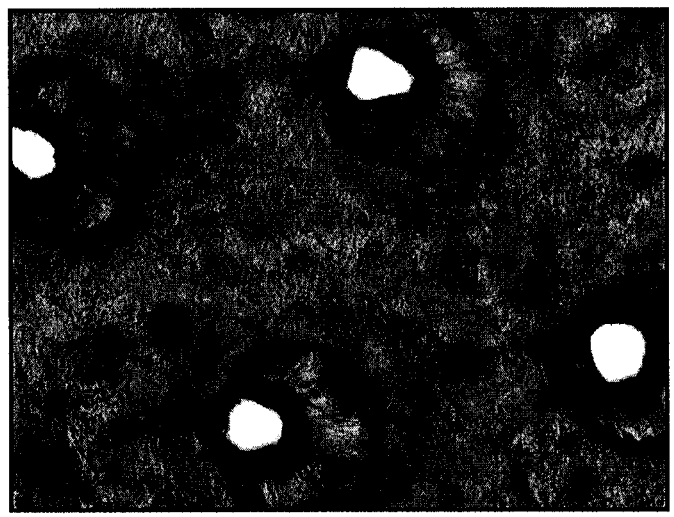
Figure 5C:
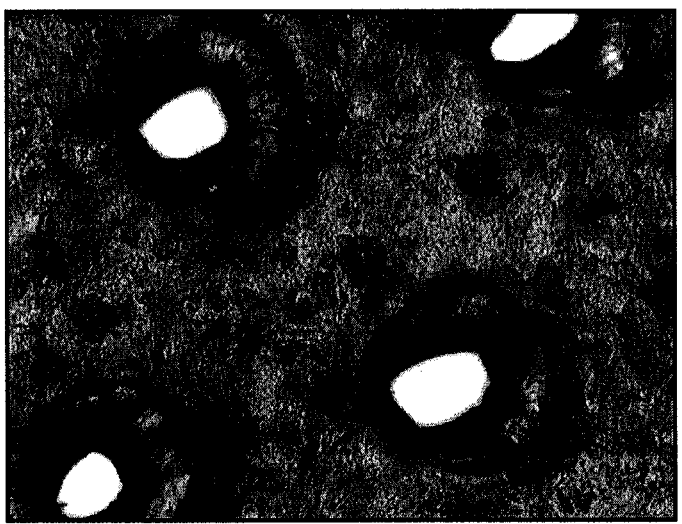

As is apparent from FIG. 5A, after 72 hours, the silicone gel completely occluded the peroration holes in the PU film. By contrast, in FIGS. 5B and 5C (otherwise same laminate and process), the deformable film [laminate of polyethylene (PE) film and polyamide (PA) film as described above] was removed after 72 hours. As can be seen from FIGS. 5B and 5C vis-à-vis FIG. 5A, implementing the step of introducing a deformable film and of keeping the deformable (or deformed) film in the perforations for at least 12 hours, preferably at least 24 hours, minimizes occlusion of the perforations by the silicone gel.

Figure 3A:
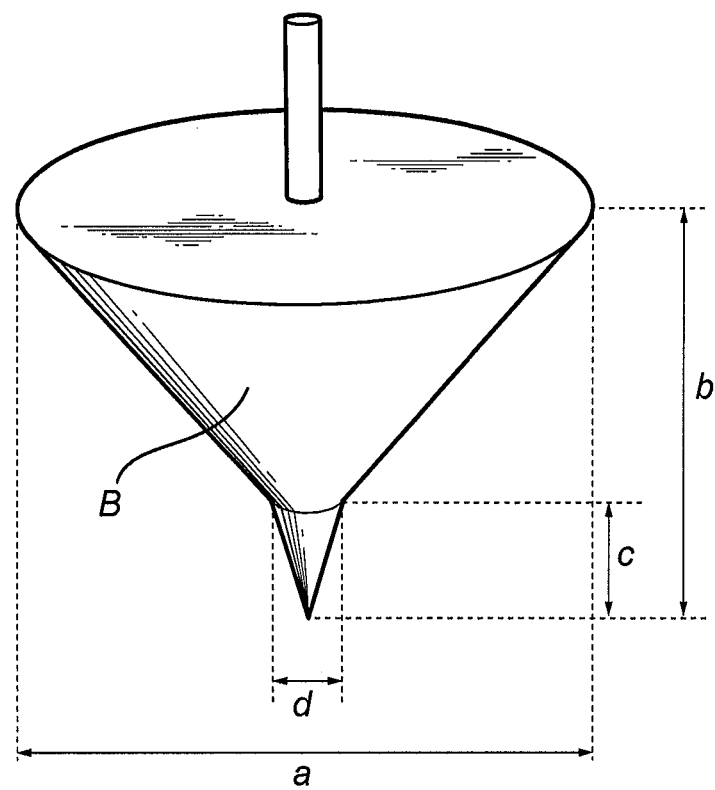
FIG. 3: shows the cone (dimension and positioning) used in the standard for measuring the softness/penetration of a given silicone gel. The measurement method is described in detail above.
Figure 3B:
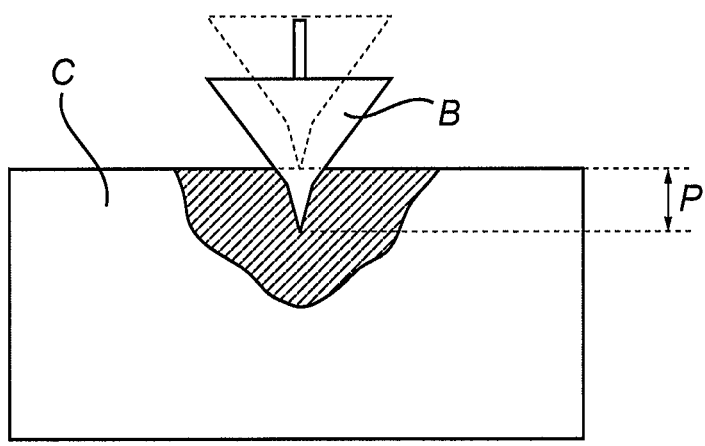
Figure 4:
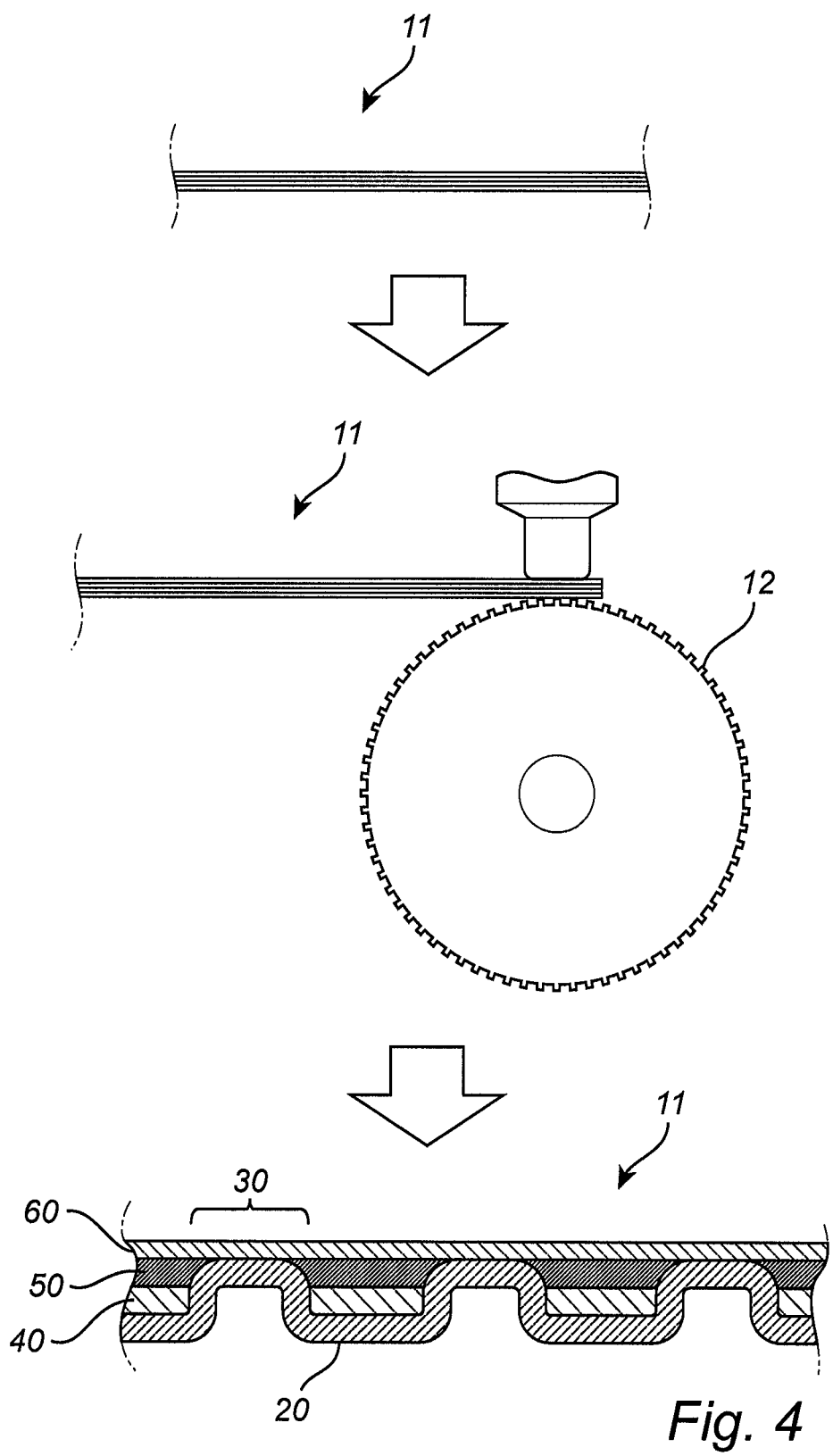
FIG. 4: illustrates the process according to an embodiment of the invention: in which a rotating drum (12) with an array of perforation elements (e.g. pins) introduces an array of perforations into a laminate (11), said laminate comprising a paper layer (60), a substrate layer (50) and a silicone layer (40), wherein a deformable film (20) (i.e. a film that can be deformed by the perforation elements but is not molten by the ultrasonic energy input) is placed in contact with the rotating drum such that the array of perforation elements create a corresponding pattern of deformed portions (or imprints) in the deformable film which deformed portions penetrate into the perforations (30) of the laminate and thereby keep any "surplus" silicone gel (40) that has been pushed away and aggregates around the edges of the perforations from occluding the perforations.
Figure 6A:
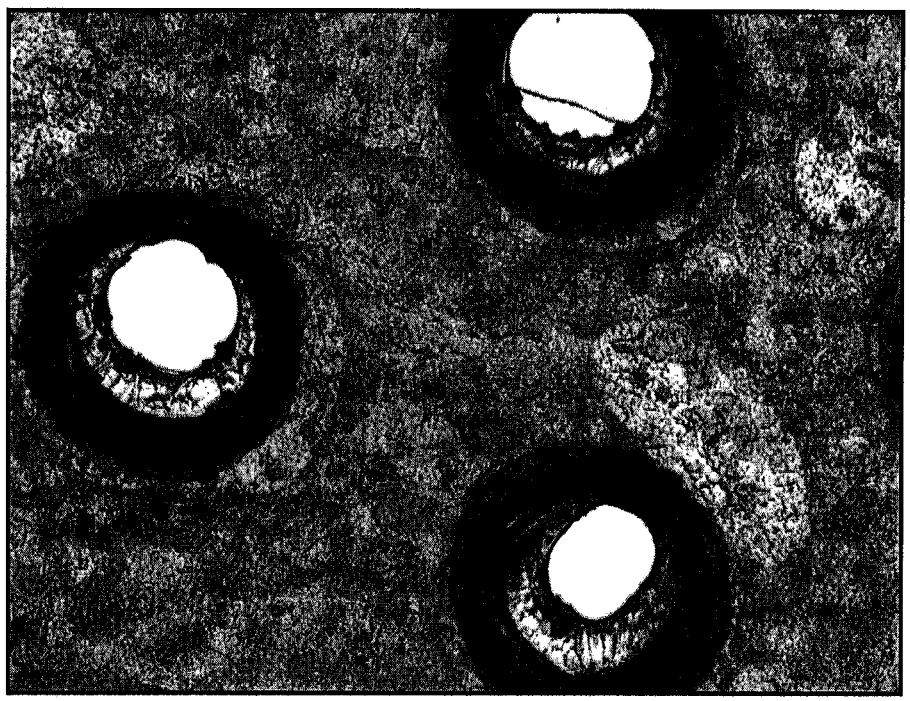
Figure 6B:
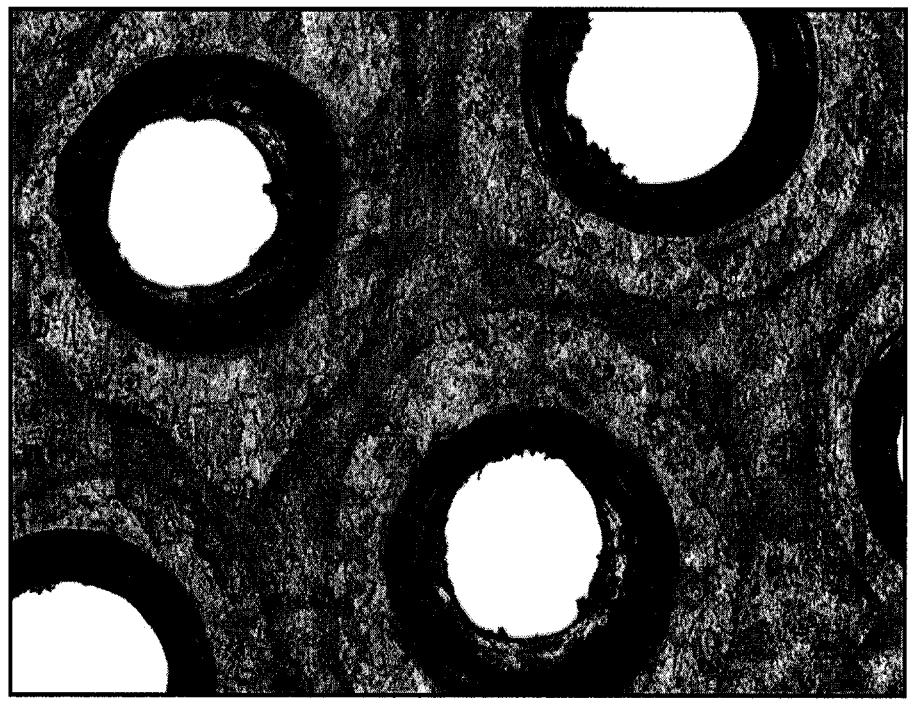

FIG. 6: shows a microscopic image of a perforated laminate having the layer structure as schematically shown in FIG. 4 (PU layer and silicone coating), wherein, in FIG. 6A, the silicone layer has a grammage of 100 g/m2 and a comparatively low softness/penetration depth of 5 mm to 6 mm, wherein the deformable film [laminate of polyethylene (PE) film and polyamide (PA) film as described above in connection with FIG. 5] as deformed and penetrating into the perforations was removed directly after the perforating step. By contrast, in FIG. 6B (otherwise same laminate and process), the deformable film [laminate of polyethylene (PE) film and polyamide (PA) film, same as above] was removed after 72 hours. As is apparent from a comparison of FIGS. 6A and 6B, the occlusion effect (i.e. movement of silicone gel into the perforations) is substantially avoided by the use of the deformable film (i.e. by keeping the deformable/deformed film after the perforation step).

All perforated products discussed above were analysed visually using polarized light microscopy. The distance between two perforations (in all analysed products) is approximately 3 mm (centre-to centre distance). All microscopic images in the above examples have been taken from the polyurethane film side of the laminate.

The invention claimed is:

1. A process for introducing a plurality of perforations into a laminate, wherein said process comprises at least the following steps:
   i. providing a laminate, said laminate comprising at least one substrate layer, said at least one substrate layer being in contact with at least one layer comprising a silicone gel:
   said laminate further comprising, in contact with said at least one layer comprising the silicone gel, at least one deformable layer;
   ii. providing an ultrasonic welding device comprising an array of perforating elements suitable for introducing perforations into at least said at least one substrate layer and said at least one layer comprising the silicone gel;
   iii. bringing said array of perforating elements in contact with said deformable layer of said laminate;
   iv. applying ultrasonic energy to said laminate in order to simultaneously introduce a plurality of perforations into at leastsaid at least one substrate layer and said at least one layer comprising the silicone gel, while introducing deformed portions in said deformable layer, wherein said deformed portions essentially correspond to the shape of the perforating elements, further wherein said deformed portions at least partly penetrate into the perforations so created;
   v. after having introduced said plurality of perforations into said laminate, keeping said deformable layer in contact with said at least one layer comprising the silicone gel, such that said deformed portions remain penetrating into said plurality of perforations, for at least 12 hours.

2. The process according to claim 1, wherein said at least one substrate layer of the laminate is a polymer layer.

3. The process according to claim 1, wherein the thickness of said at least one substrate layer is from 5 μm to 200 μm.

4. The process according to claim 1, wherein said at least one substrate layer is in contact with at least one further layer that is positioned farther away from said at least one layer comprising the silicone gel.

5. The process according to claim 1, wherein a silicone composition, precursor or silicone gel is brought into contact with the at least one substrate layer in a process step (0) that occurs prior to step (i).

6. The process according claim 5, wherein at a time from the moment of joining said at least one substrate layer with a silicone composition, precursor or silicone gel in a step (0) and the moment of applying ultrasonic energyto the laminate in orderto simultaneously introduce a plurality of perforations into said laminate is not more than 12 hours.

7. The process according to claim 1, wherein the silicone gel of the at least one layer comprising the silicone gel is based on a two-component silicone composition.

8. The process according to claim 1, wherein a softness/penetration depth of said at least one layer comprising the silicone gel is from 3 mm to 20 mm.

9. The process according to claim 1, wherein the laminate comprises an amount of said at least one layer comprising the silicone gel per squaro motor iG from 10 $g/m^2$ to 500 $g/m^2$.

10. The process according to claim 1, wherein said perforations have a diameter of from 0.5 mm to 20 mm.

11. The process according to claim 1, wherein a melting point of said deformable film is from 120 to 230° C.

12. The process according to claim 1, wherein said deformable layer comprises a material selected from the group consisting of polypropylene, polyester, polycarbonate, and polyamide or a combination thereof.

13. The process according to claim 1, wherein after keeping said deformable layer in contact with said at least one layer comprising the silicone gel, such that said deformed portions remain penetrating into said plurality of perforations, for at least 12 hours, the process further comprises the step of removing said deformable layer from said at least one layer comprising the silicone gel.

* * * * *